United States Patent [19]

Garcia

[11] Patent Number: 5,037,403

[45] Date of Patent: Aug. 6, 1991

[54] PIGTAIL CATHETER WITH ANGLED APERTURES

[75] Inventor: Gonzalo Garcia, Gladewater, Tex.

[73] Assignee: Cordis Corporation, Miami Lakes, Fla.

[21] Appl. No.: 433,671

[22] Filed: Nov. 8, 1989

[51] Int. Cl.⁵ .......................................... A61M 25/00
[52] U.S. Cl. .................... 604/280; 604/281; 128/658
[58] Field of Search .................. 604/53, 93, 264, 265, 604/280, 281; 128/656, 658

[56] References Cited

U.S. PATENT DOCUMENTS

| | | | |
|---|---|---|---|
| 2,972,779 | 2/1961 | Cowley . | |
| 3,169,527 | 2/1965 | Sheridan | 604/265 |
| 3,890,977 | 6/1975 | Wilson | 604/281 |
| 4,100,309 | 7/1978 | Micklus et al. . | |
| 4,119,094 | 10/1978 | Micklus et al. . | |
| 4,279,252 | 7/1981 | Martin | 128/658 |
| 4,579,554 | 4/1986 | Glassman | 604/102 |
| 4,594,074 | 6/1986 | Andersen et al. | 604/270 |
| 4,617,019 | 10/1986 | Fecht et al. | 604/280 |
| 4,642,267 | 2/1987 | Creasy et al. . | |
| 4,694,838 | 10/1987 | Wijayarthna et al. | 128/658 |
| 4,717,381 | 1/1988 | Papantonakos | 604/95 |
| 4,747,840 | 5/1988 | Ladika et al. | 604/280 |
| 4,755,176 | 7/1988 | Patel | 604/280 |
| 4,769,005 | 9/1988 | Ginsburg et al. | 604/53 |
| 4,784,638 | 11/1988 | Ghajar et al. | 604/264 |
| 4,863,441 | 10/1989 | Lindsay et al. | 604/264 |
| 4,887,996 | 12/1989 | Bengmark | 604/281 |

Primary Examiner—John D. Yasko
Assistant Examiner—Anthony Gutowski
Attorney, Agent, or Firm—Gerstman & Ellis, Ltd.

[57] ABSTRACT

An x-ray contrast media catheter, for example a cardiac catheter, comprises a flexible tube defining a lumen and a plurality of side apertures in the tube for fluid flow therethrough. The side apertures are each defined by a tubular surface extending through the side wall from the lumen of the exterior, in which the tubular surface defines a longitudinal axis which forms a forward angle of about 30° to 60° to the longitudinal axis of the catheter. Also, the distal end preferably defines an open aperture which, in turn, is defined by a bevelled tip of the catheter distal end. This provides improvements in the fluid flow dynamics when x-ray contrast media is being administered to a heart chamber.

6 Claims, 1 Drawing Sheet

PIGTAIL CATHETER WITH ANGLED APERTURES

BACKGROUND OF THE INVENTION

X-ray contrast media catheters are used in various medical situations to provide x-ray imagining of organs of the human body. Particularly in the field of cardiology, x-ray contrast media is applied to the heart by means of a catheter which extends therein, so that the presence of the x-ray contrast media can provide an x-ray image of the heart action and condition.

Particularly, the left ventricle is a difficult chamber of the heart to obtain x-ray imaging. At the present time, so-called pigtail catheters are used, being threaded through the aorta, around the aortic arch, and through the aortic valve until the distal tip of the catheter resides in the ventricle. Then, with the patient under an x-ray machine such as a fluoroscope, a bolus of x-ray contrast fluid is injected through the catheter at a high pressure (700-900 psi) into the ventricle, to quickly fill the ventricle with x-ray contrast media. For a moment, details of the heart structure and action become visible by x-ray imaging, until the contrast media is pumped out of the ventricle.

It has been found that, even with the best pigtail-type catheters of the prior art, difficulties have been encountered in getting good filling of the apex of the ventricle in combination with good filling of the rest of the ventricle such as the midsegmental ventricle portion. Because of this, difficulties have been obtained in obtaining accurate measurement of the ejection fraction of particularly the left ventricle. This information is critically needed for cardiologists, anesthesiologists, and surgeons as they treat heart disease.

By this invention, a catheter is provided which exhibits significant clinical improvements in the filling of heart chambers such as the left ventricle, including significantly improved apical filling. Additionally, the catheter of this invention exhibits improvements in handling and advancement through the aortic arch and the aortic valve, particularly in the situation when stenosis is present in the aortic valve.

Because of these improvements, it has become possible to obtain more accurate ejection fraction data, and to generally provide better imaging of heart structure and action, which of course provides better opportunities for accurate diagnosis and successful surgery.

DESCRIPTION OF THE INVENTION

This invention relates to an x-ray contrast media catheter, and preferably a cardiac imaging catheter, which comprises a flexible tube defining a lumen, and a plurality of side apertures in the tube for fluid flow therethrough. Typically about a dozen side apertures may be utilized in an arrangement that is generally conventional.

The side apertures are each defined by a tubular surface extending through the tube wall from the lumen to the exterior. In accordance with this invention, at least some of the tubular surfaces each define an axis which forms a forward angle of about 30° to 60° to the longitudinal axis of the catheter, and preferably about 40° to 50°.

By this modification, an improvement in the filling of body cavities, and particularly heart chambers such as the left ventricle can be achieved. Thus, a bolus of contrast fluid may be directed toward the apex of the left ventricle with improved filling. A large portion of the x-ray contrast fluid flows out of an open distal end of the catheter, but a substantial amount of contrast fluid flows out of the forward angled apertures. This forward angle allows more contrast fluid from the apertures to be projected anteriorly, when compared with conventional perpendicular apertures of the relevant prior art x-ray contrast media catheters. The forward angling of this invention allows for more deflection of contrast fluid off of body cavity walls, typically the left ventricle, for a more homogenous distribution of the contrast fluid with residual blood, which provides for better x-ray imaging. The swirling action which is provided by the forwardly angled side apertures in this invention, and the consequent angled dispersal of x-ray contrast fluid off of the ventricle walls also contributes to this significant improvement.

Typically, the side apertures used herein are rather elliptical in cross section, as is generally conventional. The combination of the forward angle of the side apertures and their elliptical cross section tends to concentrate the x-ray contrast media distally without any danger of extravasation due to its miscibility with the existing ventricular blood volume. Also, a higher percentage of contrast material provided is delivered to the ventricle, which may make possible the administration of smaller volumes of contrast material per x-ray imaging bolus provided.

It is also preferred for the catheter of this invention to define a distal end which has an open aperture, and which defines a bevelled (angled) tip about the open aperture. Such a structure provides a surprising fluid flow benefit. As the bolus of x-ray contrast fluid passes through the open tip at the distal end, because of its bevelled shape one lateral portion of the stream of fluid expelled therethrough (the outer portion relative to the longer end of the bevelled tip) exhibits more lateral flow divergence than does the opposed, lateral portion of the stream of fluid, which is next to the longer end of the bevelled tip. There turns out to be an improvement in filling the Basiler end of the left ventricle, because of this increased lateral flow divergence of the outer lateral stream portion described above. This results in good filling of the midsegmental ventricle portion, coupled with excellent filling of the apex of the ventricle.

The bevelled tip used in this invention also provides improvements in facilitating the negotiation of the distal catheter end through the aortic arch and the aortic valve with a minimization of resistance and difficulty. This feature is particularly desirable in the situation of patients who have stenosis of the aortic valve.

Preferably, the distal end of the catheter defines a spiral end that is known per se, and is commonly called a "pigtail". However, optionally by this invention, the "pigtail" is of a reduced diameter when compared with corresponding prior art catheters, having an outer diameter of about 10 to 14 mm., which is less than the normal diameter of about 16 mm. Such an improvement allows for easier maneuvering of the catheter through the aortic arch into the left ventricle, minimizing trauma, and with less likelihood of subsequent premature ventricular contractions. The tighter "pigtail" reduces "kickback" or "recoil" during the high pressure injection of contrast fluid, due to its preformed smaller diameter, and also through the improved angled or bevelled tip configuration preferably used in this invention.

It is also preferred for at least the distal end portion of the catheter of this invention to be coated with a pharmaceutically acceptable friction-reducing agent. Friction-reducing agents for catheters of various types are known. See for example Creasy et al. U.S. Pat. No. 4,642,267, and Micklus U.S. Pat. Nos. 4,119,094 and 4,100,309. Additionally, a catheter friction-reducing coating may comprise an intimate physical mixture of a major portion of a structural plastic material such as polyurethane and a minor portion of poly(ethylene oxide), typically having a molecular weight of at least about 1,000,000, with the coating being carried on the surface of the catheter. For example, a preferred coating may contain about 9 weight percent of poly(ethylene oxide) and about 91 weight percent of a polyurethane plastic.

DESCRIPTION OF SPECIFIC EMBODIMENTS

Figure 3:
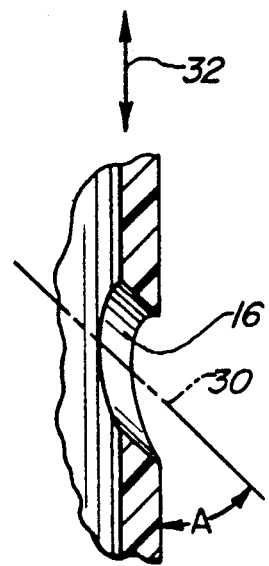
FIG. 3 is a sectional view taken along line 3—3 of FIG. 2.
Figure 1:
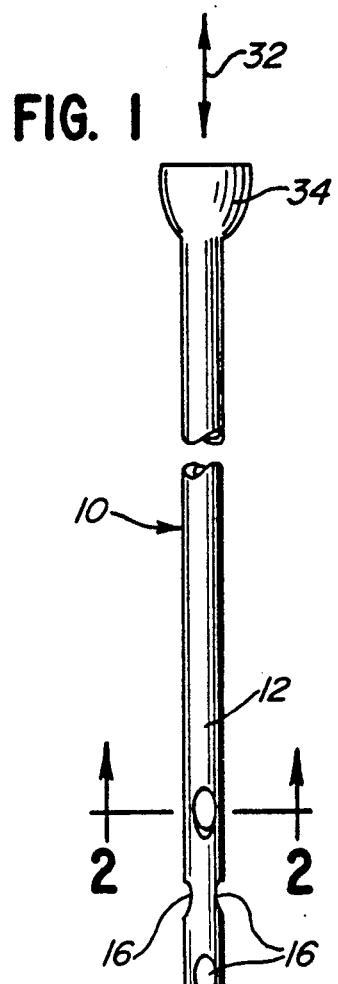
FIG. 1 is a plan view of an x-ray contrast media catheter in accordance with this invention, showing particularly details of the distal end.
Figure 2:
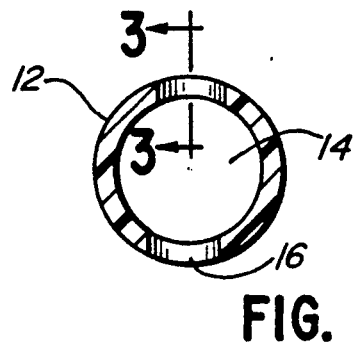
FIG. 2 is a sectional view taken along line 2—2 of FIG. 1.

Referring to the drawings, catheter 10 is a ventricular pigtail catheter for the administration of x-ray contrast media to particularly the left ventricle of the heart. Catheter 10 may be made of a physiological compatible plastic such as polyurethane or the like, and comprises a flexible tube 12 defining a lumen 14 and a plurality of side apertures 16 positioned in four staggered rows, each row being spaced 90° about the periphery of the catheter.

The distal end of catheter 10 defines a "pigtail" 18, that is to say a spiral section as shown. Distal tip 20 of the catheter defines an open end aperture 21 which is formed within tapered, aperture-defining surface 22, which exhibits a longitudinally advanced portion 24 and a longitudinally retracted portion 26 so that one wall portion 27 of the catheter extends longitudinally farther than the opposed wall portion 29.

Pigtail 18 exhibits an outer diameter 28, measured from essentially its tip diametrically across to the opposed portion as shown, which is about 12 to 13.6 cm., about 15 to 25 percent smaller than previous corresponding catheters of the prior art. The advantages of this are as described above, particularly providing improvements in the penetration through the aorta and the aortic valve.

In accordance with this invention, as shown particularly in FIG. 3, all of side apertures 16 define a tubular surface extending through tube wall 20 in which the axis 30 of each tubular surface 16 forms a forward angle A of about 45° to the longitudinal axis 32 of the catheter, and specifically the axis of that portion of catheter 10 in which the apertures 16 reside. Because of this, after the distal end 36 of the catheter has been inserted into the left ventricle, a bolus of x-ray contrast fluid may be inserted into a conventional catheter adaptor 34 at the proximal end of catheter 10 at a typical pressure of 800 psi or so. The sudden shot of x-ray contrast fluid coming out of side apertures 16 with their forward velocity components, and the shot of fluid coming out of distal tip 20, serves to better fill the ventricle with x-ray contrast media than has been previously possible with conventional catheters.

Figure 4:
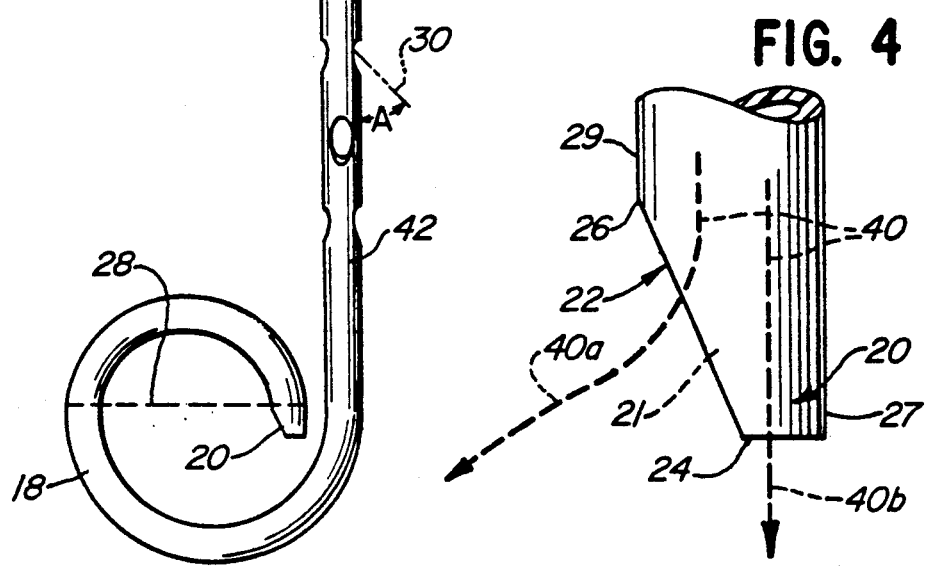
FIG. 4 is an enlarged, fragmentary, plan view of the distal tip of the catheter of this invention.

As previously discussed, the shot of x-ray contrast fluid 40 coming out of distal aperture 20 tends to exhibit an asymmetric spread because of the presence of bevelled surface 22 about aperture 21. As shown in FIG. 4, the far side 40a of the stream of x-ray contrast media which is opposed to wall 27 tends to diverge laterally outwardly to a greater degree than the near side 40b of the same stream, which is held in a more longitudinal path by the presence of longitudinally advanced wall portion 27. The advantages of this are previously discussed, and result in better and more uniform filling of the ventricle with x-ray contrast media, so that better x-ray imaging thereof is provided which, in turn, provides better measurement of ejection fractions, which are of great clinical significance in cardiology. Additionally, the bevelled surface 22 acts as a penetration aid, particularly assisting in the penetration of the aortic valve, even when stenosis is present.

Additionally, catheter 10 carries, typically at least on the outer surface of the distal 30 cm. thereof, a friction reducing agent 42 which may be a hydrophilic polymer of a type previously described. Such agents, when wetted, as takes place in the insertion of the catheter into the aorta, provide an improved slippery surface to the catheter, which greatly assists in its placement prior to applying aliquots of x-ray contrast media to the heart.

Thus, an improved catheter is provided, exhibiting significant clinical improvements which result in better data for improved diagnosis and surgery in the field of cardiology as well as other fields.

The above has been offered for illustrative purposes only, and is not intended to limit the scope of the invention of this application, which is as defined in the claims below.

That which is claimed is:

1. An x-ray contrast media catheter having a longitudinal axis, a tube wall, and a distal end, which catheter comprises a flexible tube defining a lumen, and a plurality of side apertures in the tube for fluid flow therethrough, said side apertures being each defined by a tubular surface extending through the tube wall from the lumen to the exterior, at least some of which tubular surfaces define a second longitudinal axis that forms a forward angle of about 30° to 60° to the longitudinal axis of the catheter adjacent said tubular surfaces, said distal end being in the form of a pigtail having an overall diameter of about 10mm to 14mm, said side apertures being proximal to said pigtail, said distal end defining an open aperture, whereby improved flow characteristics of x-ray contrast media are achieved for better x-ray visualization of internal organs.

2. An x-ray contrast media catheter for use in x-ray imaging of the heart, having a longitudinal axis, a tube wall, and a distal end in the form of a pigtail, which catheter comprises a flexible tube defining a lumen and a plurality of side apertures in the tube proximal to said pigtail for fluid flow through said apertures, said side apertures being each defined by a tubular surface extending through the tube wall from the lumen to the exterior, at least some of which tubular surfaces defining a second longitudinal axis that forms a forward angle of about 30° to 60° to the longitudinal axis of the catheter adjacent said tubular surfaces, the distal end of said catheter defining an aperture through a bevelled tip, whereby one lateral portion of a stream of liquid expelled therethrough exhibits more lateral flow divergence than an opposed lateral portion of said stream of liquid, and whereby improved flow characteristics of x-ray contrast media are achieved for better x-ray visualization of a heart ventricle and adjacent blood vessels.

3. The catheter of claim 2 in which said forward angle of the side apertures is about 40° to 50°.

4. The catheter of claim 2 in which said pigtail defines an overall diameter of about 10 to 14 mm..

5. The catheter of claim 2 in which at least a distal end portion thereof is coated with a pharmaceutically acceptable friction-reducing agent.

6. The catheter of claim 4 which is a ventricular x-ray imaging catheter.

* * * * *